(12) United States Patent
Oguro et al.

(10) Patent No.: US 9,329,195 B2
(45) Date of Patent: May 3, 2016

(54) CONTAINER CLEANING DEVICE, DISCHARGE MEMBER FOR CONTAINER CLEANING DEVICE, AND ANALYZER

(71) Applicant: Sysmex Corporation, Kobe-shi, Hyogo (JP)

(72) Inventors: Masahiko Oguro, Kobe (JP); Ryuichiro Ebi, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 14/527,135

(22) Filed: Oct. 29, 2014

(65) Prior Publication Data

US 2015/0125940 A1 May 7, 2015

(30) Foreign Application Priority Data

Nov. 1, 2013 (JP) .................................. 2013-228024

(51) Int. Cl.
*B08B 9/093* (2006.01)
*G01N 35/04* (2006.01)
*B01L 99/00* (2010.01)
*B08B 9/28* (2006.01)

(52) U.S. Cl.
CPC ................ *G01N 35/04* (2013.01); *B01L 99/00* (2013.01); *B08B 9/28* (2013.01); *B01L 2200/026* (2013.01); *B01L 2300/0858* (2013.01); *B01L 2400/049* (2013.01); *G01N 2035/0437* (2013.01)

(58) Field of Classification Search
CPC .................. B08B 9/093; B08B 9/928; G01N 2035/0437; B01L 3/02; B01L 3/021; B01L 3/022
See application file for complete search history.

(56) References Cited

U.S. PATENT DOCUMENTS

| 7,252,803 B2* | 8/2007 | Guthrie ..................... B01L 7/00 159/6.1 |
| 2003/0132109 A1* | 7/2003 | Bullen .................... B01L 3/021 204/403.01 |
| 2009/0260661 A1* | 10/2009 | Lindros ............... B05B 15/0258 134/167 R |
| 2010/0132438 A1* | 6/2010 | Burkard ............. G01N 35/1011 73/64.53 |

* cited by examiner

*Primary Examiner* — Brian R Gordon
(74) *Attorney, Agent, or Firm* — Brinks Gilson & Lione

(57) ABSTRACT

Disclosed is a container cleaning device which cleans a container for holding a sample. The device comprises: a container holding section for holding the container which has a substantially spherical inner bottom; a discharge section which is inserted into the container; and a cleaning nozzle which discharges a cleaning liquid into the container. The discharge section comprises an aperture at the bottom, and comprises a discharge flow path which is connected to the aperture and discharges the sample or the cleaning liquid in the container, and the discharge section is insertable to the deepest part of the container, and the bottom part of the discharge section conforms to the shape of the substantially spherical inner bottom of the container.

14 Claims, 18 Drawing Sheets

CONTAINER CLEANING DEVICE, DISCHARGE MEMBER FOR CONTAINER CLEANING DEVICE, AND ANALYZER

RELATED APPLICATIONS

This application claims priority under 35 U.S.C. §119 to Japanese Patent Application No. 2013-228024 filed on Nov. 1, 2013, the entire content of which is hereby incorporated by reference.

FIELD OF THE INVENTION

The present invention relates to a container cleaning device which cleans containers that have held samples including biological samples, and an analyzer, and a discharge member used in the container cleaning device.

BACKGROUND OF THE INVENTION

There are conventional analyzers which clean the containers that have held samples (for example, refer to United States Patent Application Publication No. 2010/0126536).

United States Patent Application Publication No. 2010/0126536 discloses an analyzer provided with a cleaning device which includes an suctioning nozzle for suctioning liquid in a cuvette, and a supplying nozzle for supplying cleaning liquid into a cuvette, wherein the cross sectional areas of the suctioning nozzle and the supplying nozzle are greater than the cross sectional area of the internal diameter. In this analyzer, when the suctioning nozzle and the supplying nozzle are inserted in a cuvette, the sum of the volume of the submerged part of the supplying nozzle and the volume of the submerged part of the suctioning nozzle is greater than the volume of the liquid within the cuvette, hence, reducing the amount of cleaning liquid required for cleaning.

SUMMARY OF THE INVENTION

In United States Patent Application Publication No. 2010/0126536, however, since the tubular suctioning nozzle and tubular supplying nozzle are configured to be inserted into a squared tubular cuvette, the distance between the inner wall surface of the cuvette and the outer surface of the suctioning nozzle is not uniform in the cross section of the cuvette, thus preventing uniform cleaning of the inside of the cuvette. In order to reduce so-called carry over, in which sample remains in the cuvette prior to cleaning and is carried over to the measurement of the next sample, cleaning must be performed until the part at which the cleaning force is weakest (that is, the part of greatest distance between the inner wall surface of the cuvette and the outer surface of the suctioning nozzle) is sufficiently clean, thus causing concern that the total amount of cleaning liquid (amount used) that is ultimately used cannot be reduced.

The container cleaning device of the first aspect of the present invention is a container cleaning device which cleans a container for holding a sample, comprising: a container holding section for holding the container which has a substantially spherical inner bottom; a discharge section which is inserted into the container; and a cleaning nozzle which discharges a cleaning liquid into the container. The discharge section comprises an aperture at the bottom, and comprises a discharge flow path which is connected to the aperture and discharges the sample or the cleaning liquid in the container; and the discharge section is insertable to the deepest part of the container, and the bottom part of the discharge section conforms to the shape of the substantially spherical inner bottom of the container.

In the container cleaning device of the first aspect, it is preferable that a channel is formed in the bottom of the discharge section when the discharge section is inserted to the deepest part of the container, the cleaning liquid or sample flowing in the channel.

In this case, it is preferable that the channel is configured to guide the sample or cleaning liquid to the aperture.

In such a configuration, it is preferable that the discharge section comprises a plurality of channels; and the plurality of channels respectively connect to the aperture.

When configured with a plurality of channels, it is preferable that the aperture is positioned at or in the vicinity of the bottom end of the discharge section, and that the plurality of channels extend radially at substantially equiangular intervals around the aperture.

When sample or cleaning liquid is guided to the aperture by such channels, it is preferable that the discharge section comprises a body portion, wherein a side surface of the body portion is substantially parallel to an inner wall surface of the container, and the channel is formed to extend from the aperture to the vicinity of the end part on the bottom side of the body portion.

In this channel configuration, it is preferable that a width of the channel is less than the inner diameter of the aperture of the discharge section in planar view.

In the container cleaning device of the first aspect, it is preferable that the gap between the inner wall surface of the container and the bottom part of the discharge section inserted into the container becomes narrower toward the deepest end of the container.

In the container cleaning device of the first aspect, it is preferable that the discharge section includes an inclined section shaped as a conical frustum with an external diameter that is tapered upward, and the cleaning nozzle is configured to discharge cleaning liquid so as to flow along this inclined section shaped as a conical frustum when the discharge section is inserted in the container.

In the container cleaning device of the first aspect, it is preferable that an elevator device configured to uplift the discharge section to insert the discharge section into the container, and to lower the discharge section to remove the discharge section from the container; wherein the discharge flow path is configured to discharge the sample into the container as the discharge section is lowered by the elevator device.

In this case, it is preferable that the cleaning nozzle is configured to discharge the cleaning liquid when the discharge section is lifted by the elevator device so that the discharge section is distanced upward from the deepest part of the container, and the discharge section is lowered to the deepest part of the container by the elevator device after the cleaning liquid is discharged.

In this configuration wherein the cleaning nozzle discharges cleaning liquid into the container when the discharge section has been lifted up from the deepest part of the container by the elevator device, it is preferable that the discharge flow path is configured to discharge the cleaning liquid into the container while the discharge section is being lowered by the elevator device.

In the container cleaning device of the first aspect, it is preferable that the discharge flow path is integratedly formed with the discharge section.

In the container cleaning device of the first aspect, it is preferable that the discharge flow path is a tubular nozzle, and this nozzle is fixedly inserted in the discharge section so as to connect to the aperture.

In this configuration provided with an elevator device to raise and lower the discharge section for insertion in the container, it is preferable that the container is a cylindrical container which has a substantially spherical inner bottom, the discharge section has a substantially circular horizontal cross section, and the elevator device inserts the discharge section into the cylindrical container so that the center axis of the discharge section matches the center axis of the cylindrical container.

In this configuration, it is preferable that the sample is derived from a biological sample collected from a subject.

The discharge member of the container cleaning device of a second aspect of the present invention is a discharge member for a container cleaning device for cleaning a container set in the container device. The container has a substantially spherical inner bottom and being for holding a sample. The discharge member comprising: a discharge section comprising an aperture at the bottom part and inserted into the container; a discharge flow path disposed on the discharge section and connected to the aperture to discharge a liquid in the container. The discharge section is configured to be insertable to the deepest part of the container, and the bottom part of the discharge section is formed to conform to the substantially spherical inner bottom of the container.

The analyzer of a third aspect of the present invention is provided with a sample preparing section for preparing a measurement sample by conducting in a container a predetermined processing of a biological sample collected from a subject; a measuring section for measuring the measurement sample; and a container cleaning device. The container cleaning device comprises: a container holding section for holding the container which has a substantially spherical inner bottom; a discharge section which is inserted into the container; and a cleaning nozzle which discharges a cleaning liquid into the container. The discharge section comprises an aperture at the bottom, and comprises a discharge flow path which is connected to the aperture and discharges the measurement sample or the cleaning liquid in the container; and the discharge section is insertable to the deepest part of the container, and the bottom part of the discharge section conforms to the shape of the substantially spherical inner bottom of the container.

DETAILED DESCRIPTION OF THE PREFERRED EMBODIMENTS

Figure 1:
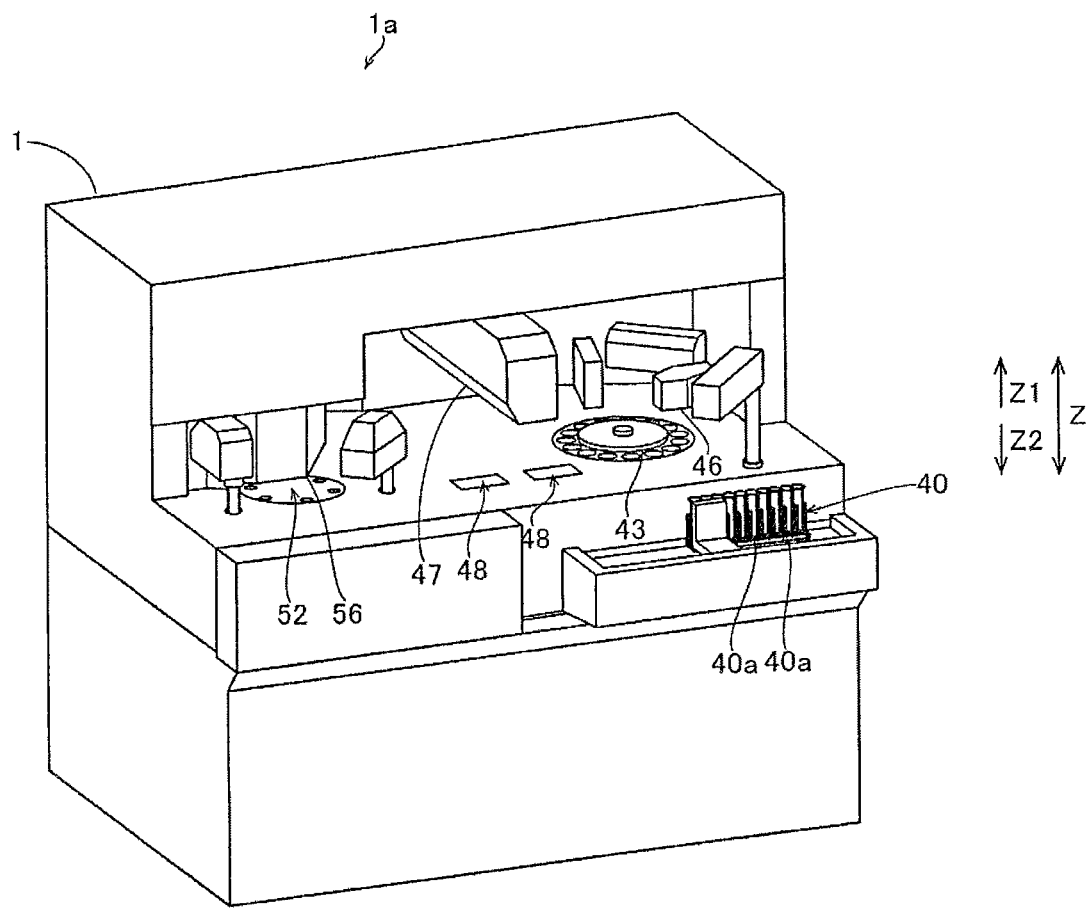
FIG. 1 is a perspective view showing the general structure of the cell analyzer of an embodiment of the present invention.

The embodiments are described below based on the drawings.

The structure of the cell analyzer 1a of an embodiment is described below with reference to FIGS. 1 through 14. The cell analyzer 1a is an apparatus for analyzing uterine epithelial cells to screen for uterine cancer using flow cytometry.

The cell analyzer 1a induces a measurement sample containing cells collected from a patient to flow through a flow cell (not shown in the drawing), and irradiates the measurement sample with laser light as the sample flows through the flow cell. The scattered light and fluorescent light from the measurement sample are detected and analyzed to determine whether there are cancer cells among the cells.

Figure 2:
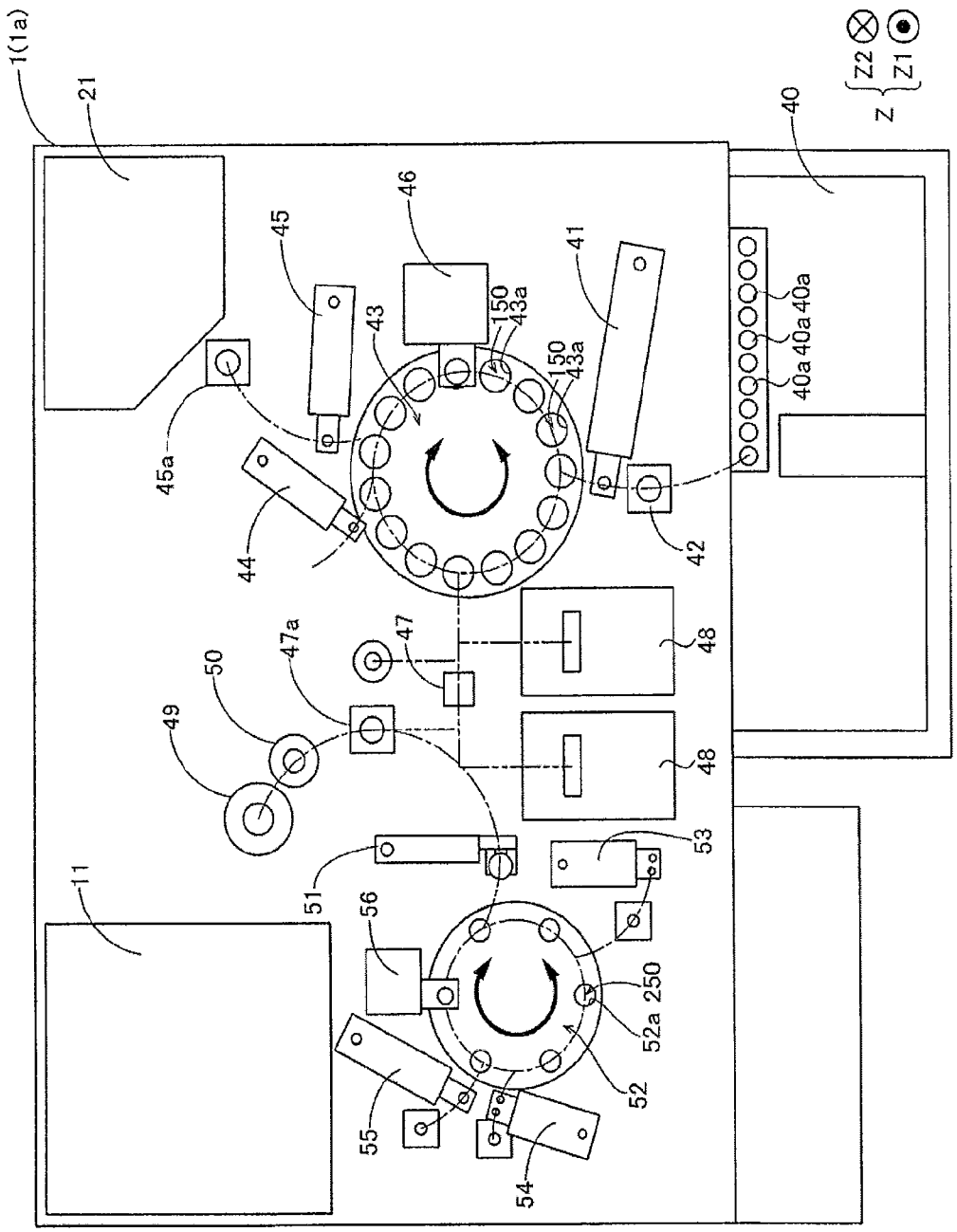
FIG. 2 is a schematic view showing the planar arrangement of each part of the cell analyzer of the embodiment of the invention.

As shown in FIGS. 1 and 2, the cell analyzer 1a has a measuring device 1 which uses laser light to optically measure a measurement sample prepared by processing a biological sample collected from a patient through a cell dispersion process and staining process, and a data processing device 2 (refer to FIG. 3) which analyzes the measurement results obtained by the measuring device 1.

Figure 3:
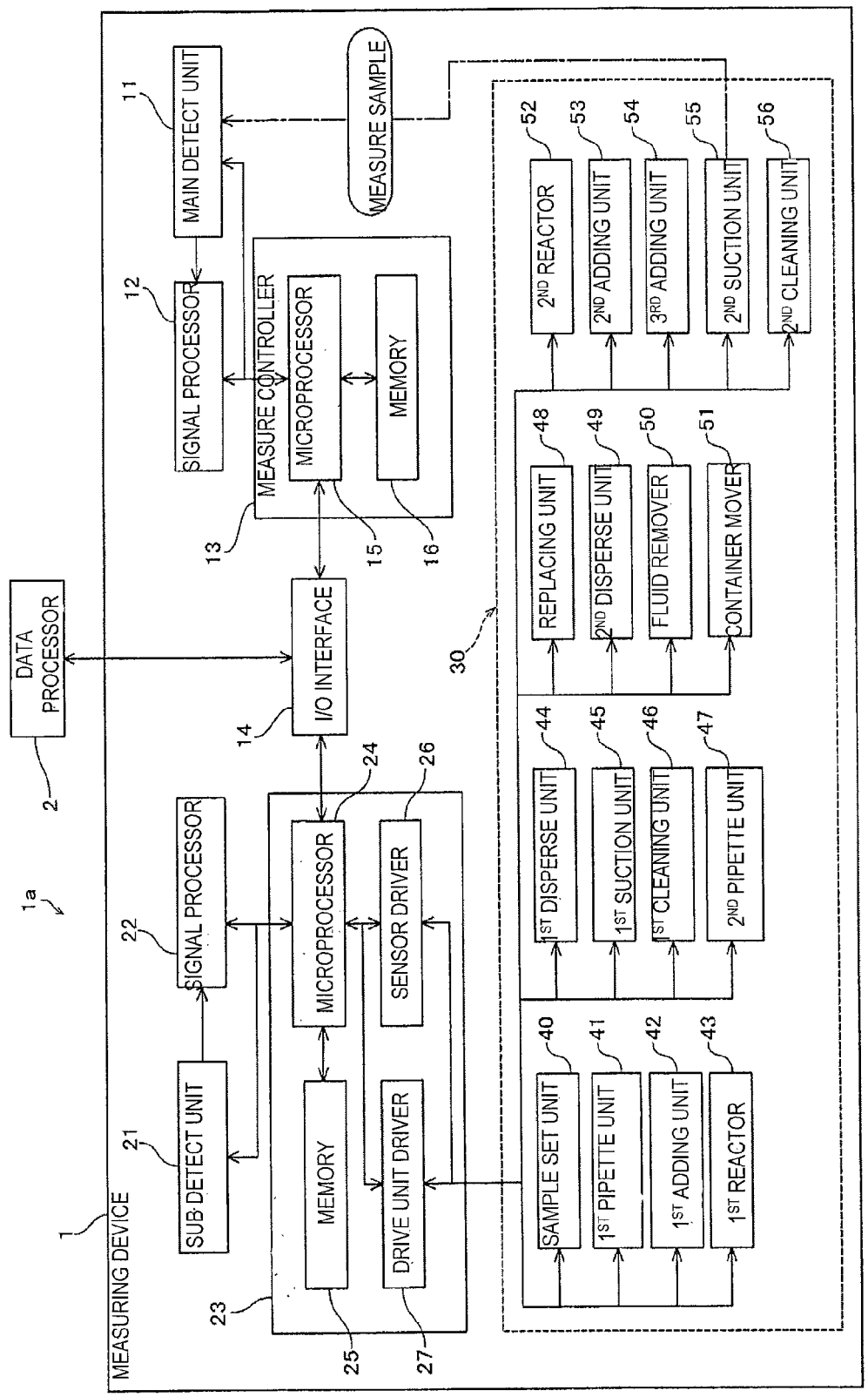
FIG. 3 is a block diagram showing the each part of the cell analyzer of the embodiment of the present invention.

As shown in FIG. 3 the measuring device 1 has a main detecting section 11, signal processing section 12, measurement controller 13, and I/O interface 14. The measuring device 1 also includes a sub detecting section 21, signal processing section 22, preparation controller 23, and preparation device 30 which automatically performs component preparation of the biological sample.

The main detecting section 11 has the function of detecting measurement target cells for example, (epithelial cells of the cervix), the number of nuclei, and size of the cells from the measurement sample. The main detecting section 11 uses a flow cytometer (not shown in the drawing). The main detecting section 11 is configured to irradiate the cells with light to obtain (detect) the forward scattered light (FSC), side scattered light (SSC), and side fluorescent light (SFL)). The data processing section 2 determines whether the measurement target cells are abnormal, and specifically atypical cells based on the FSC, SSC, and SFL obtained by the main detecting section 11.

The signal processing section 12 performs the required signal processing of the output signals from the main detecting section 11. The measurement controller 13 includes an MPU (microprocessor) 15, and memory unit 16. The memory unit 16 is configured by a ROM and RAM for storing the control program and data of the main detecting section 11.

The measurement controller 13 and MPU 15 are connected to the data processing device 2 and the MPU 24 (described later) of preparation controller 23 through the I/O interface 14.

The sub detecting section 21 has the function of counting the number of cells (hereinafter referred to as "cell concentration") per unit volume of the measurement target cells prior to the main measurement by the main detecting section 11. The amount of biological sample and stock solution needed to prepare the measurement sample to be used in the main measurement is determined based on the results of the sub detection. A flow cytometer identical to the flow cytometer of the main detecting section 11 is used in the sub detecting section 21. The signal processing section 22 performs the required signal processing of the output signals from the sub detecting section 21. The preparation controller 23 includes an MPU 24, memory unit 25, sensor driver 26, and drive section driver 27. The MPU 24 is connected to the data processing device 2 and the MPU 15 of the measurement controller 13 through the I/O interface 14. The memory unit 25 is configured by a ROM and RAM for storing the control program and the like for controlling the sub detecting section 21 and preparation device section 30. Note that detailed description of the sub detecting section 21 is omitted since the structure is identical to that of the main detecting section 11.

The preparation device section 30 has a sample set unit 40, first sample pipette unit 41, first reagent preparing unit 42, first reaction unit 43, first dispersing unit 44, first sample suction unit 45, and first container cleaning section 46. The preparation device unit 30 includes a second sample pipette unit 47, replacement unit 48, second dispersing unit 49, liquid removal unit 50, container mover 51, second reaction unit 52, second reagent adding unit 53, third reagent adding unit 54, second sample suction unit 55, and second container cleaning section 56.

As shown in FIGS. 1 and 2, the sample set unit 40 accepts a plurality of sample containers 40a that hold a mixture of a sample and a stock solution which has methanol as the main component. The sample set unit 40 has the function of sequentially transporting the received sample containers 40a to the biological sample suctioning position of the first sample pipette unit 41.

The first sample pipette unit 41 has the function of transferring (dispensing) the biological sample in the sample container 40a and the dispersion liquid (described later) of the first reagent preparing unit 42 to the first container 150 held in the first reaction unit 43, as shown in FIG. 2. Note that the first container 150 has a substantially spherical inner bottom.

The dispersion liquid (for example, a solution containing N-acetyl-L-cysteine (NAC)) to be added to the biological sample is prepared and kept in the first reagent preparing unit 42.

The first reaction unit 43 has the function of promoting the reaction between the dispersion liquid and the biological sample in the first container 150. As shown in FIG. 2, the first reaction unit 43 is configured by a circular rotating table capable of rotating in clockwise and counterclockwise directions. A plurality of holders 43a which can hold the first container 150 are provided on the peripheral margin of the rotating table.

The first dispersing unit 44 has the function of initiating in the biological sample the first dispersion process (shearing process) for dispersing the aggregated cells in the biological sample.

The first sample suctioning unit 45 has the function of dispensing the biological sample subjected to the first dispersion process to the holder 45a. The sub detecting unit 21 then detects the number of measurement target cells are in the biological sample which has been dispensed to the holder 45a.

In the present embodiment, the first container cleaning section 46 makes the first container 150 reusable by cleaning the inside of the first container 150 after the first sample suctioning unit 45 supplies the measurement sample to the sub detecting unit 21 via the second detection pipette 47. Details of the first container cleaning section 46 are described later.

As shown in FIGS. 2 and 3, the second sample pipette unit 47 has the function of supplying the biological sample within the first container 150 held in the first reaction unit 43 to the replacement unit 48, and the function of supplying the concentrate which was concentrated in the discrimination/replacement unit 48 to the second container 250 disposed in the sample transfer unit 47a. The second container 250 is smaller than the first container 150 (for example, a cuvette). Note that the second container 250 has a substantially spherical inner bottom.

The replacement unit 48 has the function of receiving the biological sample after the first dispersion process by the first dispersing unit 44, and replacing the methanol based stock solution with a diluting liquid. The replacement unit 48 also has the function of discriminating the measurement target cells from other cells contained in the biological sample, and the function of preparing concentrate containing a concentration of detectable cancer cells.

The second dispersing unit 49 has the function of performing the second dispersion process (ultrasonic dispersion process) on the biological sample which has been treated by predetermined processing by the replacement unit 48.

The liquid removal unit 50 has the function of removing water adhered to the outer surface of the second container 250 after the second dispersing process by the second dispersing unit 49.

The container mover 51 holds the second container 250, and has the function of moving the second container 250 to the sample transfer unit 47a, second dispersing unit 49, liquid removal unit 50, and second reaction unit 52.

The second reaction unit 52 has the function of promoting the reaction between the biological sample in the second container 250 and the reagents added by the second reagent adding unity 53 and the third adding reagent unit 54. The second reaction unit 52 is configured by a circular rotating table capable of rotating in clockwise and counterclockwise directions. A plurality of holders 52a which can hold the second container 250 are provided on the peripheral margin of the rotating table.

The second reagent adding unit 53 is configured to add a predetermined amount of RNase to the second container 250 for RNA processing of cells. The third reagent adding unit 54 is configured to add a predetermined amount of staining liquid (for example, propidium iodide solution) to the second container 250 to stain the cell nuclei. The measurement sample to be measured by the main detecting section 11 is prepared in this way.

The second sample suction unit 55 has the function of suctioning the measurement sample within the second container 250 set in the second reaction unit 52, and transferring the measurement sample to the main detecting section 11. The measurement sample transferred by the second sample suctioning unit 55 is measured by the main detecting section 11 to determine if atypical cells are present.

In the present embodiment, the second container cleaning section 56 makes the second container 250 reusable by cleaning the inside of the second container 250 after the measurement sample is supplied to the main detecting unit 11. Details of the second container cleaning section 56 are described later.

Figure 6:
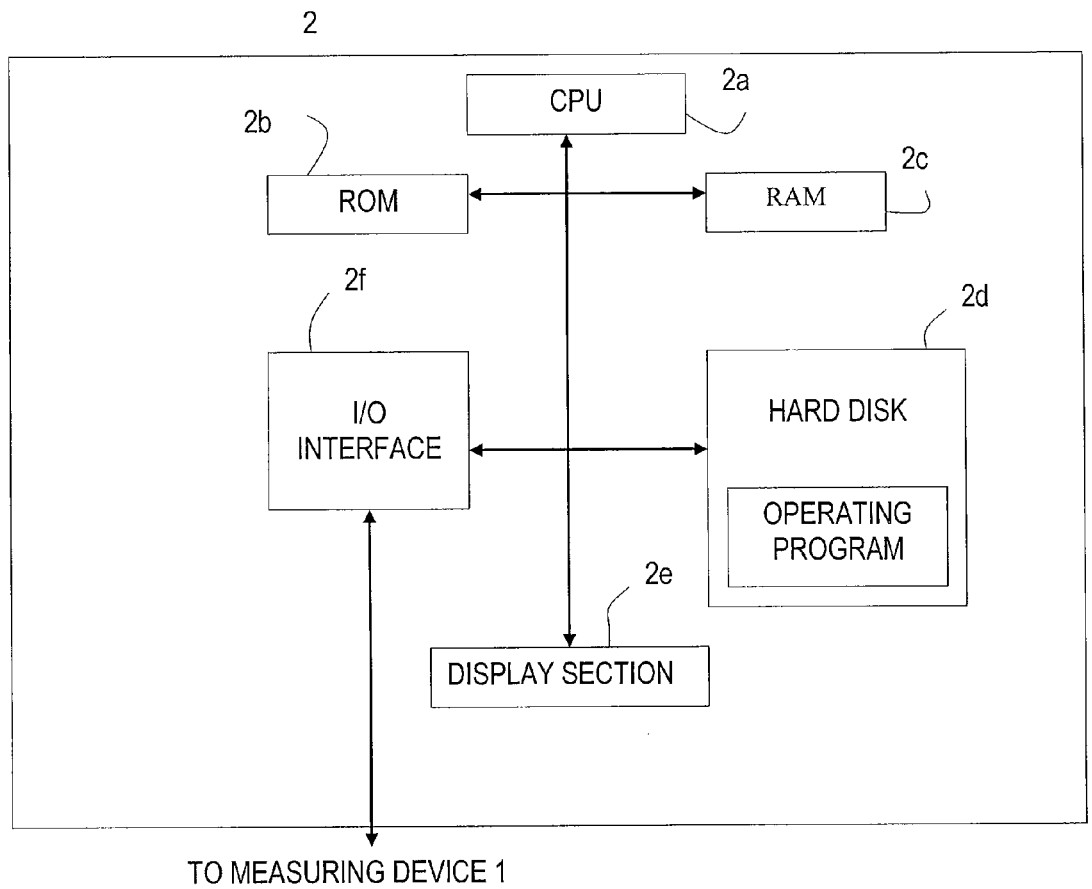
FIG. 6 is a block diagram showing the data processing device of the cell analyzer of the embodiment of the present invention.

The data processing device 2 is configured by, for example, a personal computer (not shown in the drawings). As shown in FIG. 6, the data processing device 2 has a CPU 2a, ROM 2b, RAM 2c, hard disk 2d for storing various programs, display section 2e, and I/O interface 2f. The data processing device 2 is connected to the I/O interface 14 of the measuring device 1 through the I/O interface 2f, and is configured to send and receive data bidirectionally with the measurement device 1.

The structures of the first container cleaning section 46 and the second container cleaning section 56 are described in detail below.

Figure 7:
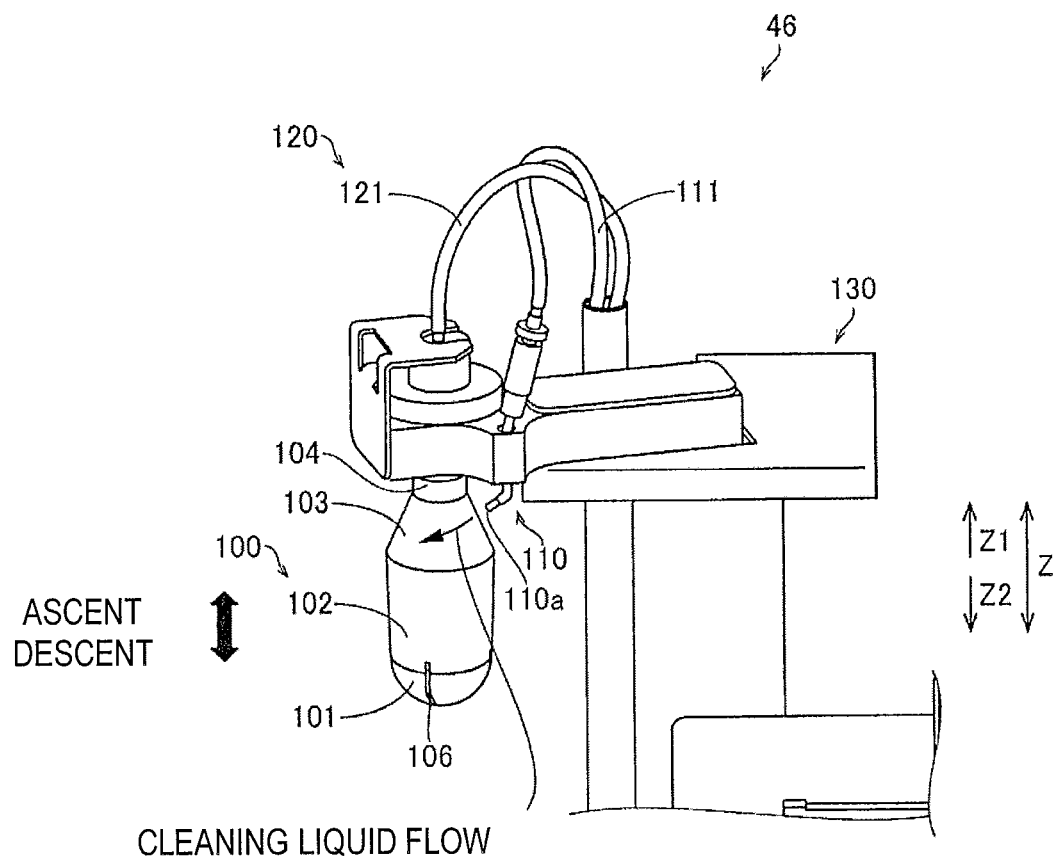
FIG. 7 illustrates the elevator device of the first container cleaning section of the cell analyzer of the embodiment of the present invention.

The first container cleaning section 46 has the function of cleaning the inside (inner wall surface 150a, refer to FIG. 9) of the cylindrical first container 150, as shown in FIG. 7. The first container cleaning section 46 is provided with a discharge member 100, discharge device 110, suction device 120, and elevator device 130. The discharge member 100 includes sequentially from below (Z2 direction) a bottom portion 101, body portion 102, and inclined portion 103. The discharge member 100 also includes a discharge flow path 107 (refer to FIG. 9). The discharge member 100 is made of resin, and the constituent portions are integratedly formed. The discharge member 100 is somewhat smaller than the interior part of the first container 150. There is a gap between the discharge member 100 and the inner wall surface 150a of the first container 150. The sample and cleaning liquid circulates through this gap to the deepest part 150b of the first container 150. The discharge member 100 has a substantially circular horizontal cross section.

Figure 8:
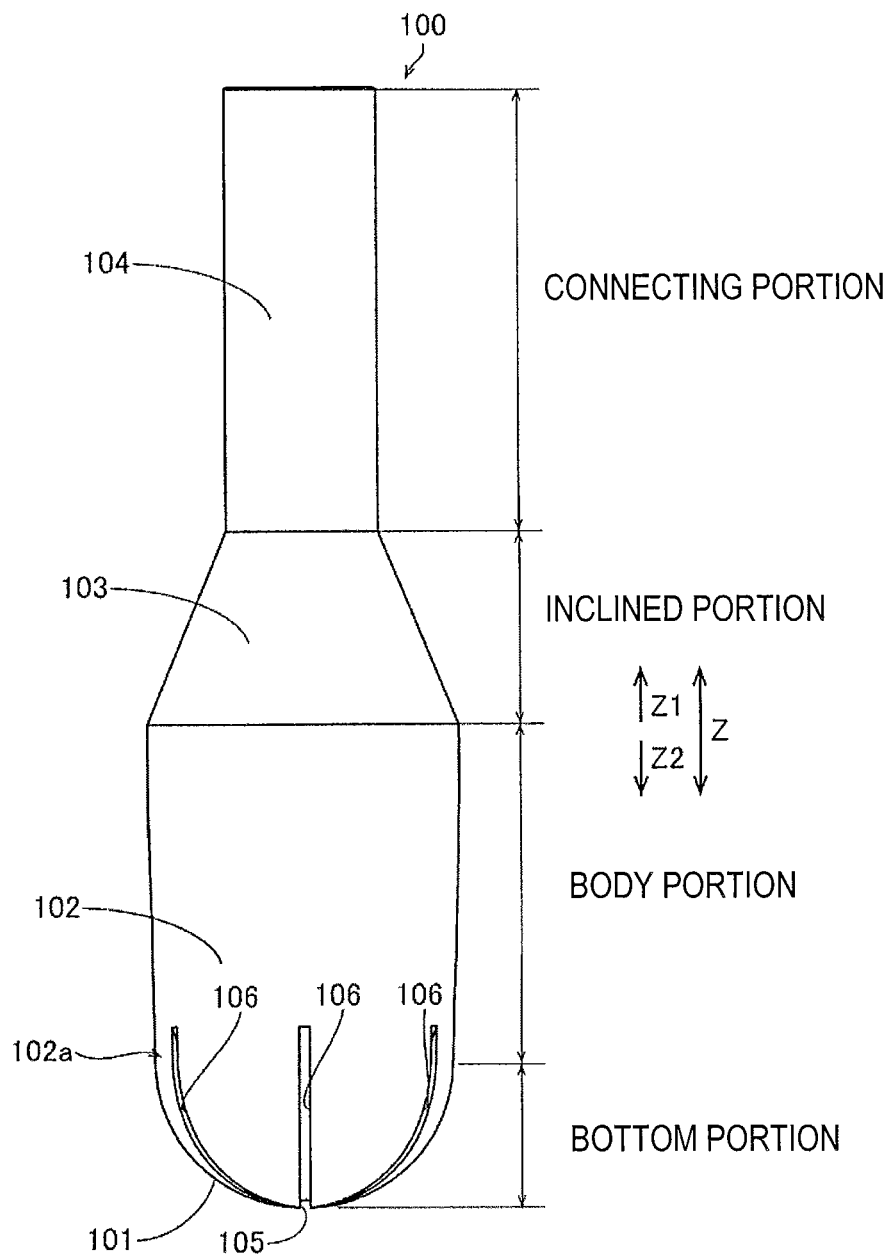
FIG. 8 shows the first container cleaning section of the cell analyzer of the embodiment of the present invention.
Figure 9:
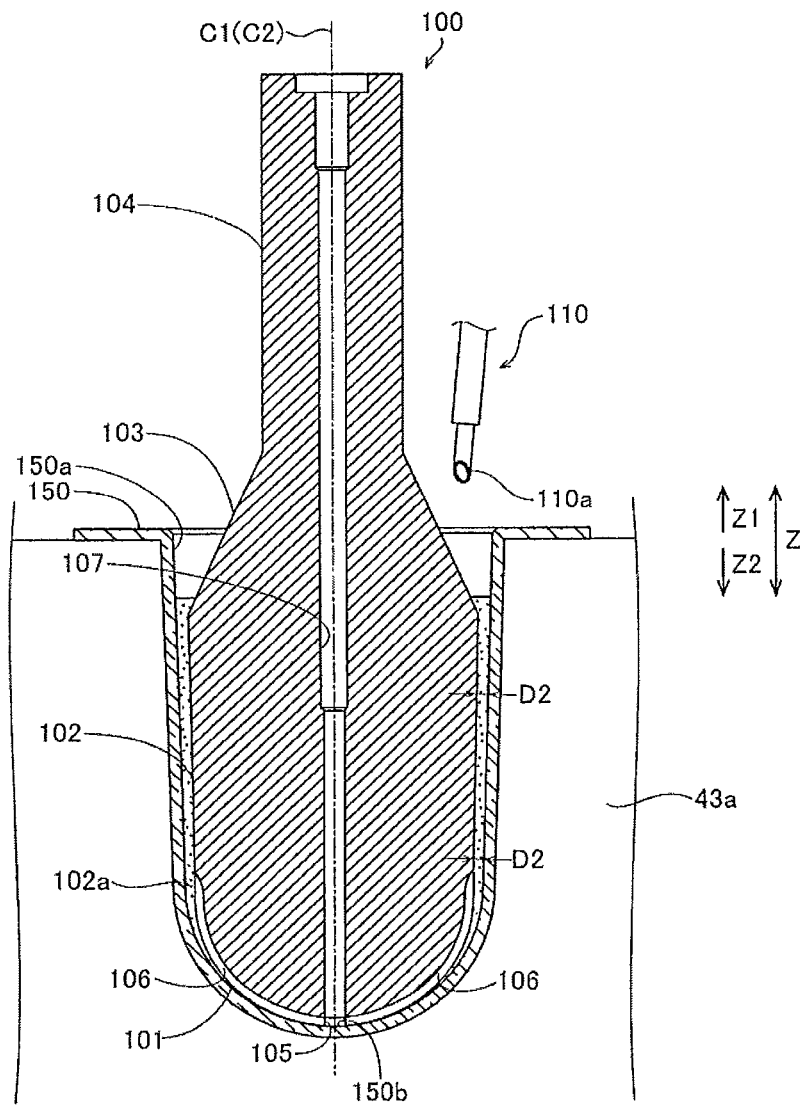
FIG. 9 shows the discharge member inserted in the first container of the cell analyzer of the embodiment of the present invention.

The bottom portion 101 is substantially hemispherical in shape and protrudes downward (Z2 direction), as shown in FIGS. 8 and 9. The bottom portion 101 has a shape corresponding to the shape of the inner wall surface 150a of the first container 150. That is, the surface of the bottom portion 101 has a shape which conforms to the shape of the inner wall surface 150a (briefly, a shape similar to the shape of the inner wall surface 150a). The discharge member 100 is configured to be insertable to the deepest part 150b of the first container 150, and the bottom part 101 is shaped to conform to the spherical inner bottom of the first container 150. The bottom portion 101 is provided with an aperture 105 and a plurality (six) of channels 106 (refer to FIG. 11).

Figure 11:
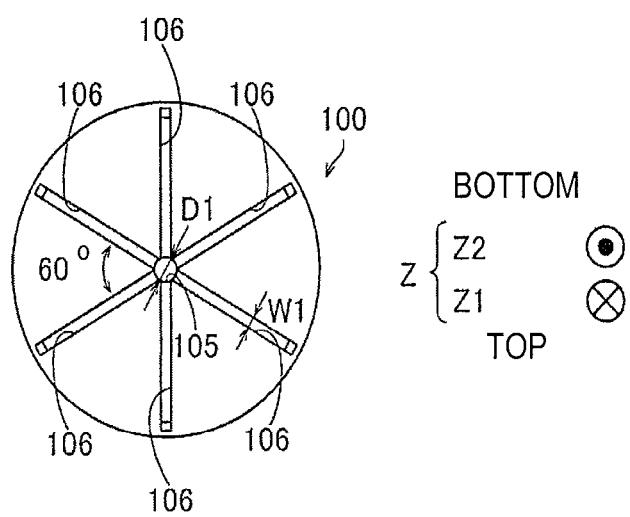
FIG. 11 is a view from the bottom side of the discharge member of the first container cleaning section of the cell analyzer of the embodiment of the present invention.

As shown in FIG. 11, the aperture 105 is provided substantially at the center of the bottom part 101 in planar view. The aperture 105 has a substantially circular shape. The aperture 105 is provided at the bottom end of the discharge member 100. The bottom end of the discharge member 100 is configured to make contact with the deepest part 150b of the first container 150, as shown in FIG. 9.

As shown in FIGS. 8 and 9, the channels 106 are configured so as to extend from the aperture 105 across the body portion 102 to the vicinity of the end part 102a on the bottom portion 101 side (Z2 direction). The discharge member 100 is configured so that the gap between the bottom portion 101 inserted into the first container 150, and the inner wall surface 150a of the first container 150 gradually narrows toward the deepest part 150b of the first container 150. The channels 106 are configured so that the sample or cleaning liquid flows and is guided to the aperture 105 when the discharge member 100 is inserted into the deepest part 150b of the first container 150. Specifically, the six channels 106 are connected to the aperture 105, as shown in FIG. 11. The six channels 106 extend radially at substantially equiangular intervals (60 degrees) around the aperture 105. The channels 106 have a width W1 which is smaller than the internal diameter D1 of the aperture 105 of the discharge member 100 in planar view. The channels 106 extend substantially linearly.

As shown in FIG. 9, the body portion 102 is configured to extend parallel to the inner wall surface 150a of the first container 150. That is, there is a constant interval D2 between the surface of the body portion 102 and the inner wall surface 150a of the first container 150.

The inclined portion 103 is formed at the position of the discharge member 100 corresponding to the vicinity of the top end of the first container 150 when the discharge member 100 is inserted in the first container 150. The inclined portion 103 also is formed in a conical frustum shape wherein the external diameter of the discharge member 100 tapers upward toward the center (direction of the discharge flow paths 107) of the discharge member 100. The discharge member 100 also is mounted on the elevator device 130 through a connector 104.

The discharge flow paths 107 are tubular discharge holes provided in the discharge member 100. The discharge flow paths 107 extend vertically (Z direction). The discharge flow paths 107 communicate with (are connected to) the aperture 105, and are configured to discharge the sample or cleaning liquid contained in the first container 150.

The discharge device 110 is configured to switchably discharge distilled water and diluting liquid as cleaning liquid to the first container 150. Note that diluting liquid is a liquid prepared under osmotic pressure which does not damage the cells.

Figure 10:
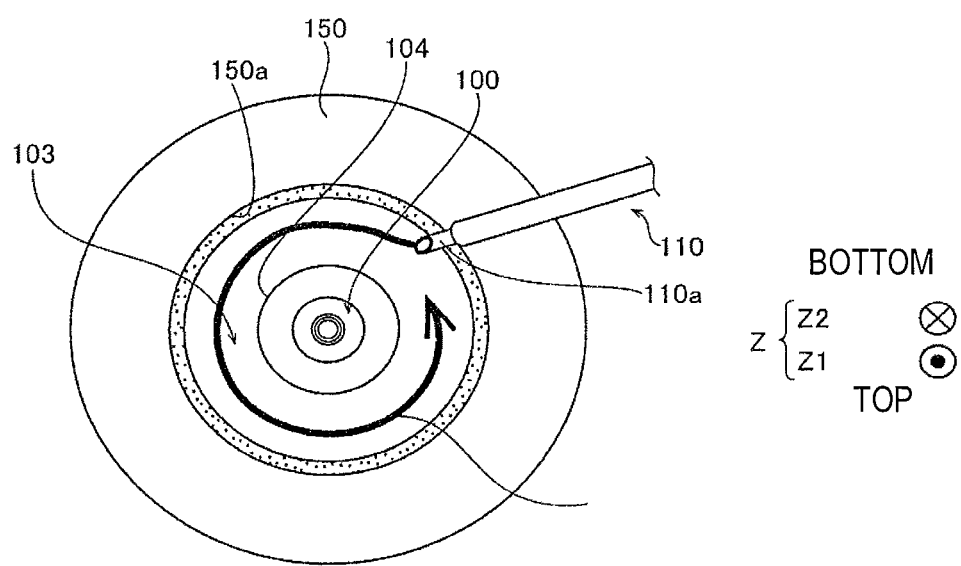
FIG. 10 illustrates the cleaning liquid flowing along the inclined section of the cell analyzer of the embodiment of the present invention.

The discharge device 110 has a discharge portion 110a, supply tube 111, and switch control valve 113 (refer to FIG. 4), as shown in FIG. 7. The discharge device 110 is operationally controlled by the fluid controller 114. The supply tube 111 is supplied with distilled water and diluting liquid from a distilled water reservoir and diluting liquid reservoir not shown in the drawing. The fluid controller 114 switches the liquid discharged from the discharge portion 110a between distilled water and diluting liquid by controlling the switch control valve 113. As shown in FIG. 9, the discharge portion 110a is provided at a position which is substantially the same height as the inclined portion 103 of the discharge member 100. The discharge device 110 is configured to discharge cleaning liquid so as to flow along conical frustum shaped inclined portion 103 when the discharge member 100 is inserted in the first container 150. Thus, the cleaning liquid circulates around the discharge member 100 and fills the inside of the first container 150, as shown in FIG. 10.

The suctioning device 120 includes a discharge tube 121, suction sensor 122 (refer to FIG. 4), and suction control valve 123 (refer to FIG. 4), as shown in FIG. 7. The suction device 120 is operationally controlled by the fluid controller 114 (refer to FIG. 4). The suction device 120 is connected to the aperture 105 through the discharge flow path 107 of the discharge member 100, as shown in FIG. 9. The suction sensor 122 is an optical sensor, and is configured to detect sample or cleaning liquid flowing within the discharge tube 121 suctioned by the suction device 120.

Figure 4:
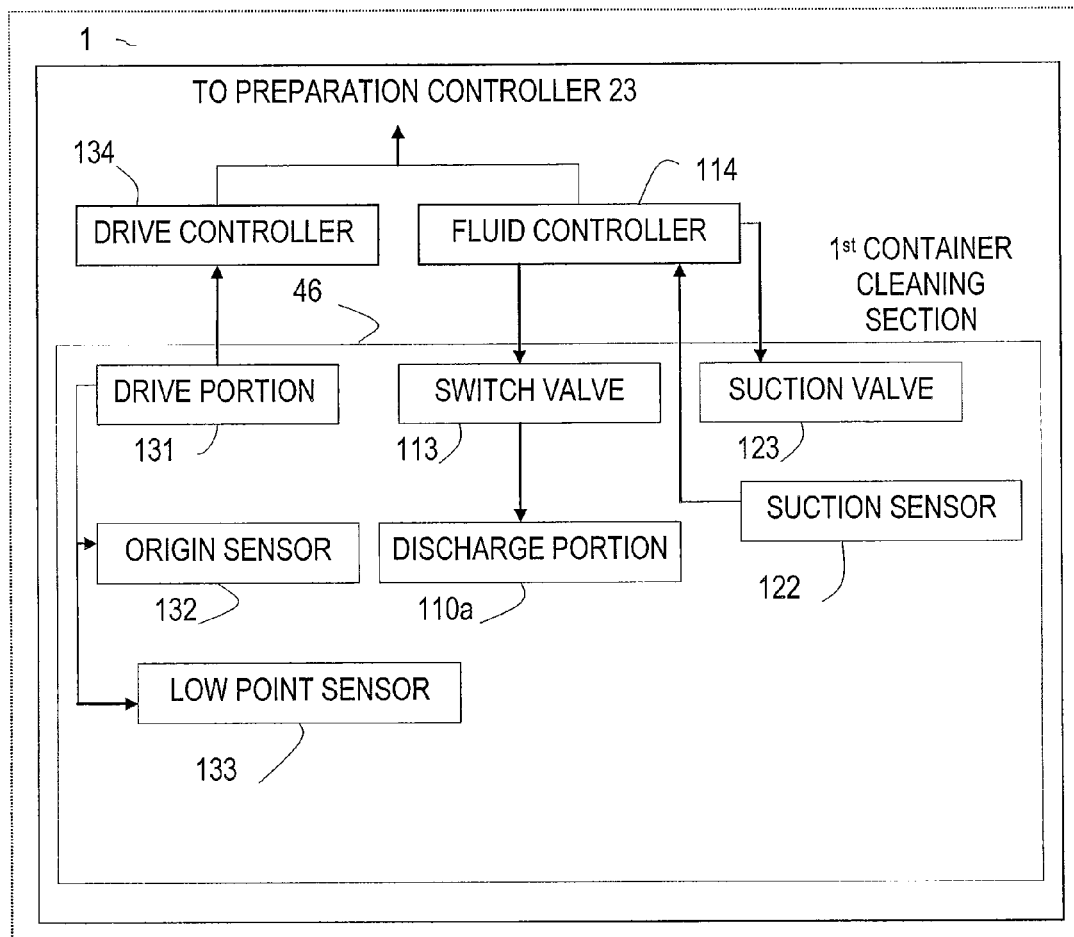
FIG. 4 is a block diagram showing the first container cleaning section of the cell analyzer of the embodiment of the present invention.

The elevator device 130 has a drive portion 131, origin sensor 132, and low point sensor 133, as shown in FIG. 4. The drive portion 131 is operationally controlled by a drive controller 134. As shown in FIG. 7, the drive portion 131 is configured to vertically raise and lower the discharge member 100. The discharge member 100 thus can be inserted into the first container 150 and removed from the first container 150. As shown in FIG. 9, the discharge member 100 is configured lowered (inserted) to the deepest part 150b of the first container 150. The origin sensor 132 is configured to detect discharge member 100 at the origin position (upper limit position of the movable discharge member 100). The low point sensor 133 is configured to detect the discharge member 100 at the lowest position (position at which the discharge member 100 contacts the deepest part 150b of the first container 150). Note that the discharge member 100 can be easily inserted into the first container 150 by configuring the center axis C1 (axis through the center of the vertical cross section) of the first container 150 and the center axis C2 of the discharge member 100.

The structure of the second container 150 is described in detail below. Note that since the structure of the second container cleaning section 56 is identical to the structure of the first container cleaning section 46, detailed description is omitted.

Figure 12:
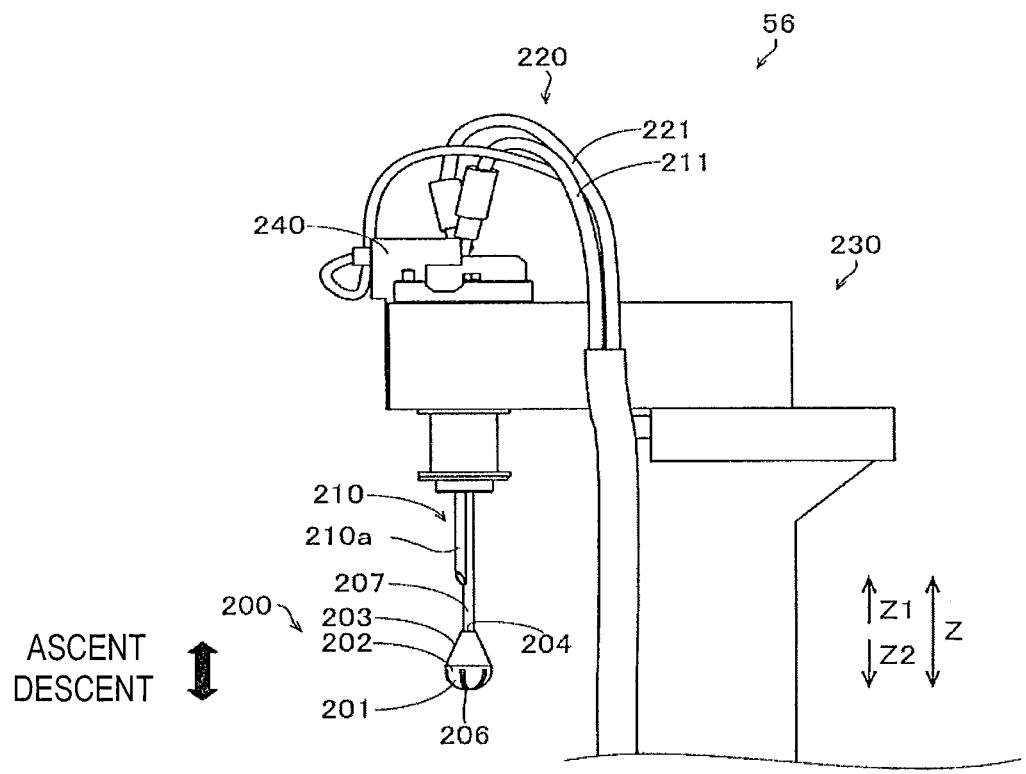
FIG. 12 illustrates the elevator device of the second container cleaning section of the cell analyzer of the embodiment of the present invention.

The second container cleaning section 56 has the function of cleaning the inside (inner wall surface 250a, refer to FIG. 13) of the second container 250, as shown in FIG. 12. The second container 250 has a substantially teardrop shape. The second container cleaning section 56 is provided with a discharge member 200, discharge device 210, suction device 220, and elevator device 230. The second container cleaning section 56 also has a sensor 240 for detecting that the discharge member 200 is not missing from the second container cleaning section 56. The discharge member 200 includes sequentially from below a bottom portion 201, body portion 202, inclined portion 203, and hole 204. The discharge member 200 is integratedly formed of resin.

Figure 14:
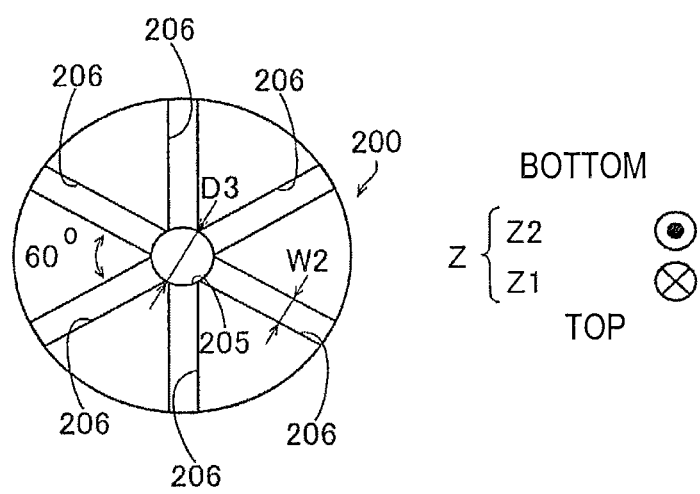
FIG. 14 is a view from the bottom side of the discharge member of the second container cleaning section of the cell analyzer of the embodiment of the present invention.

The bottom portion 201 has a shape corresponding to the shape of the inner wall surface 250a of the second container 250. That is, the surface of the bottom portion 201 has a shape which conforms to the shape of the inner wall surface 250a (briefly, a shape similar to the shape of the inner wall surface 250a). The bottom portion 201 is provided with an aperture 205 and a plurality (for example, six) of channels 206. The channels 206 are from the aperture 205 to the vicinity of the end part 202a of the body portion 202 on the bottom portion 201 side. The bottom end of the discharge member 200 is configured to come into contact with the deepest part 250b of the second container 250. As shown in FIG. 14, the channels 206 have a width W2 which is smaller than the inner diameter D3 of the aperture 205 of the discharge member 200 in planar view.

A tube 207 is fixedly inserted (for example, press-fitted) in the hole 204 of the discharge member 200. The tube 207 extends vertically. The tube 207 communicates with (is connected to) the aperture 205, and is configured to discharge the sample or cleaning liquid contained in the second container 250.

There is a constant interval D4 between the surface of the body portion 202 and the inner wall surface 250a of the second container 250.

The inclined portion 203 is provided at the position facing the inner wall surface 250a of the second container 250 when the discharge member 200 is inserted in the second container 250.

The discharge device 210 has a discharge portion 210a, supply tube 211, and switch control valve 213 (refer to FIG. 5), as shown in FIG. 12. The discharge device 210 is operationally controlled by the fluid controller 214 (refer to FIG. 5). The discharge device 210 is disposed so that the discharge portion 210a is above the inclined portion 203 of the discharge member 200. The discharge portion 210a is substantially parallel to the tube 207. The discharge device 210 is configured to discharge cleaning liquid (distilled water) toward (Z2 direction) the inclined portion 203 when the discharge member 200 is inserted in the second container 250.

Figure 13:
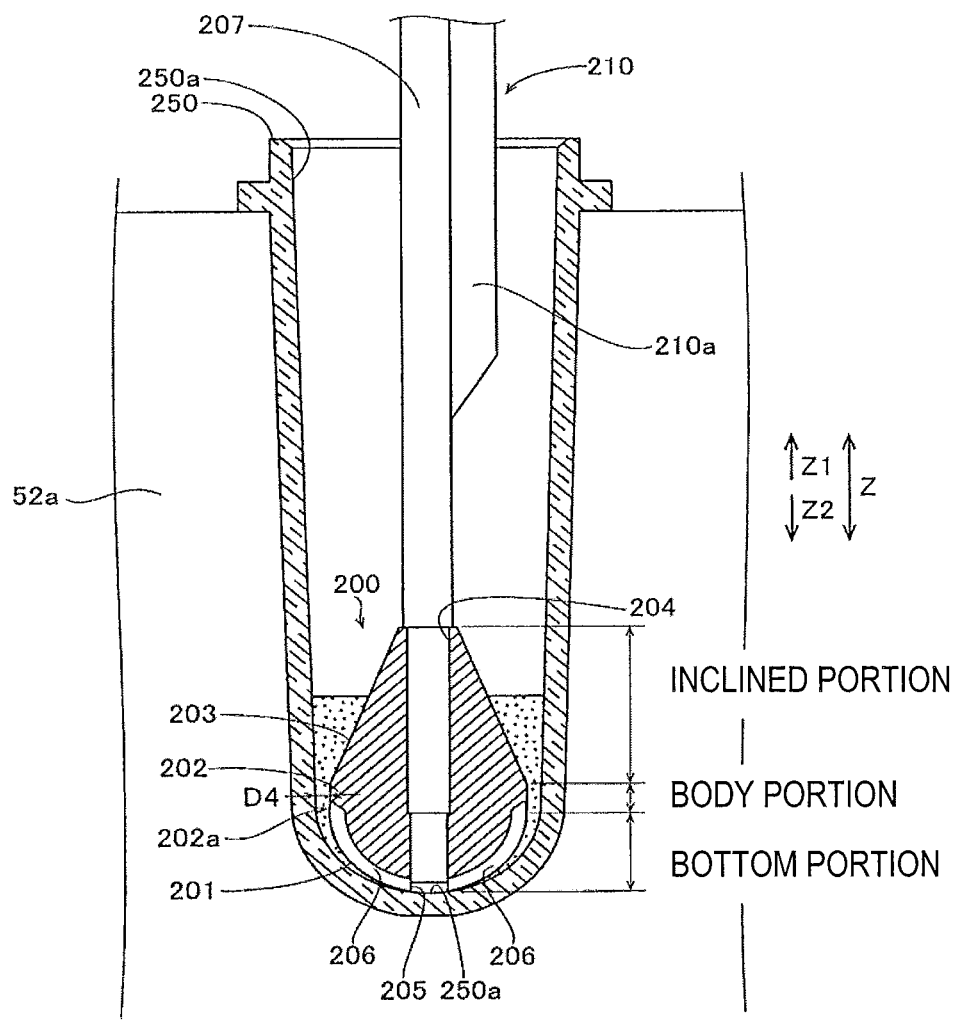
FIG. 13 shows the discharge member inserted in the second container of the cell analyzer of the embodiment of the present invention.

The suctioning device 220 includes a discharge tube 221, suction sensor 222 (refer to FIG. 5), and suction control valve 223 (refer to FIG. 5), as shown in FIG. 12. The suction device 220 is operationally controlled by the fluid controller 214. The suction device 220 is connected to the aperture 205 through the tube 207 of the discharge member 200, as shown in FIG. 13.

Figure 5:
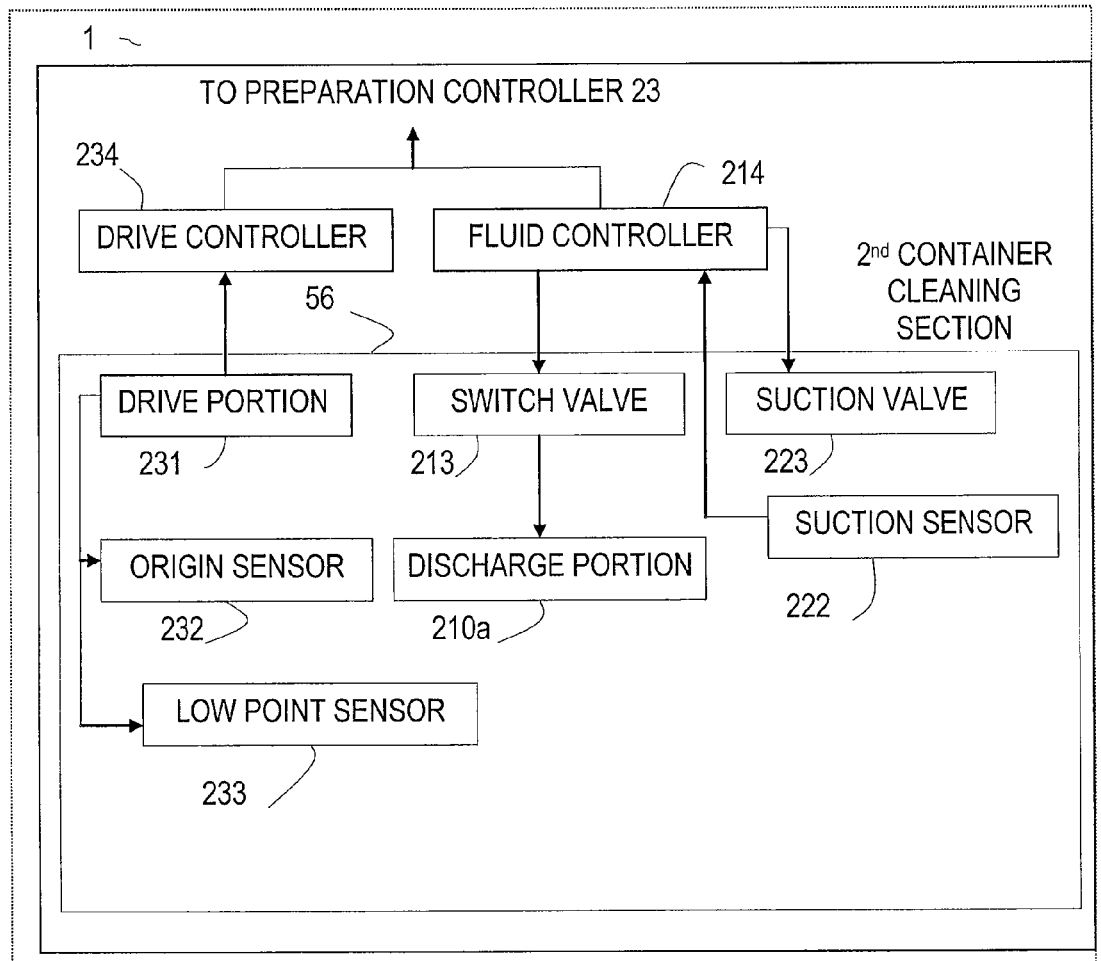
FIG. 5 is a block diagram showing the second container cleaning section of the cell analyzer of the embodiment of the present invention.

The elevator device 230 has a drive portion 231, origin sensor 232, and low point sensor 233, as shown in FIG. 5. The elevator device 230 (drive portion 231) is operationally controlled by a drive controller 234.

Figure 15:
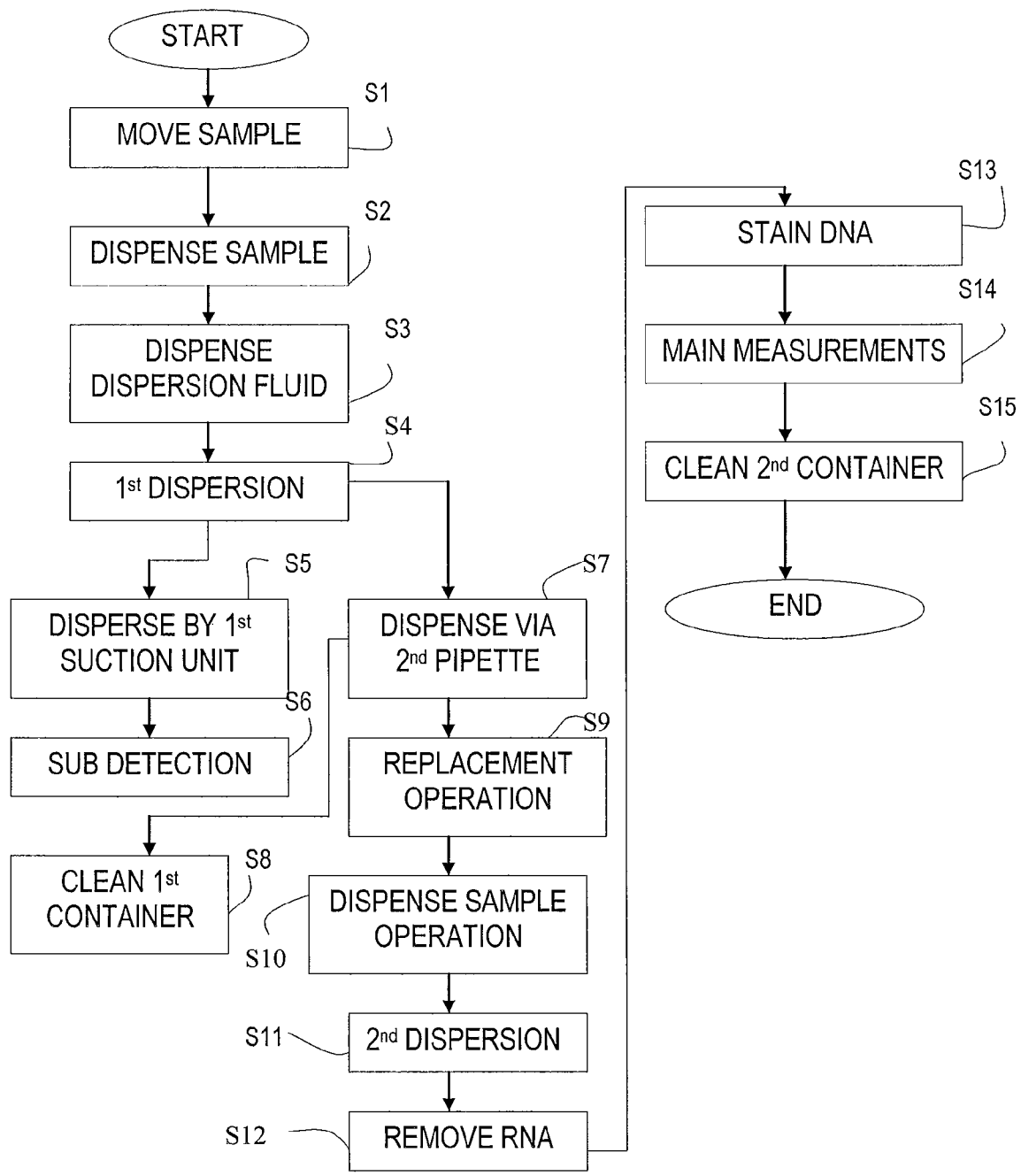
FIG. 15 is a flow chart describing the cell analysis process of the cell analyzer of the embodiment of the present invention.

The cell analysis process of the cell analyzer 1a is described below with reference to FIGS. 2, 3, and 15. Note that operational control of the main detecting section 11 and signal processing section 12 of the measuring device 1 is executed by the measurement controller 13 (MPU 15), an operation control of the sub detecting section 21, signal processing section 22, and preparation device section 30 of the measuring device 1 is executed by the preparation controller 23 (MPU 24). The control of the data processing device 2 is executed by the CPU 2a.

In step S1, the preparation controller 23 sequentially moves the sample containers 40a held in the sample set section 40 to the biological sample suctioning position via the sample pipette unit 41.

In step S2, the preparation controller 23 dispenses the biological sample from the sample container 40a to the first sample pipette unit 41. Specifically, the preparation controller 23 aspirates the biological sample from the sample container 40a to the first sample pipette 41, and discharges the sample to the first container 150 disposed in the first reaction unit 43.

In step S3, the preparation controller 23 dispenses dispersion liquid to the first sample pipette 41. Specifically, the preparation controller 23 suctions the dispersion liquid (NAC) from the first reagent preparing unit 42 via the first sample pipette 41, and discharges the dispersion liquid into the first container 150 to which the biological sample was previously dispensed.

In step S4, the preparation controller 23 controls the first dispensing unit 44 to perform the first dispensing process. After step S4, processing branches to a process to execute sub detection of the biological sample (steps S5 and S6), and a main process for performing the main detection (step S7 and subsequent steps). In step S5, the preparation controller 23 causes the first sample suctioning unit 41 to dispense the biological sample to the holder 45a.

In step S6, the preparation controller 23 controls the sub detecting section 21 to perform sub detection.

In step S7, the preparation controller 23 dispenses the biological sample to the second sample pipette 47. Specifically, after the biological sample is dispensed to the first sample suction unit 45 in step S5, the preparation controller 23 rotates the first reaction unit 43 counterclockwise, and moves the first container 150 to a position for aspirating the biological sample via the second sample pipette unit 47. The preparation controller 23 suctions a predetermined amount of the biological sample by the second sample pipette 47 based on the results of the sub detection, and discharges the sample to the replacement unit 48.

Figure 16:
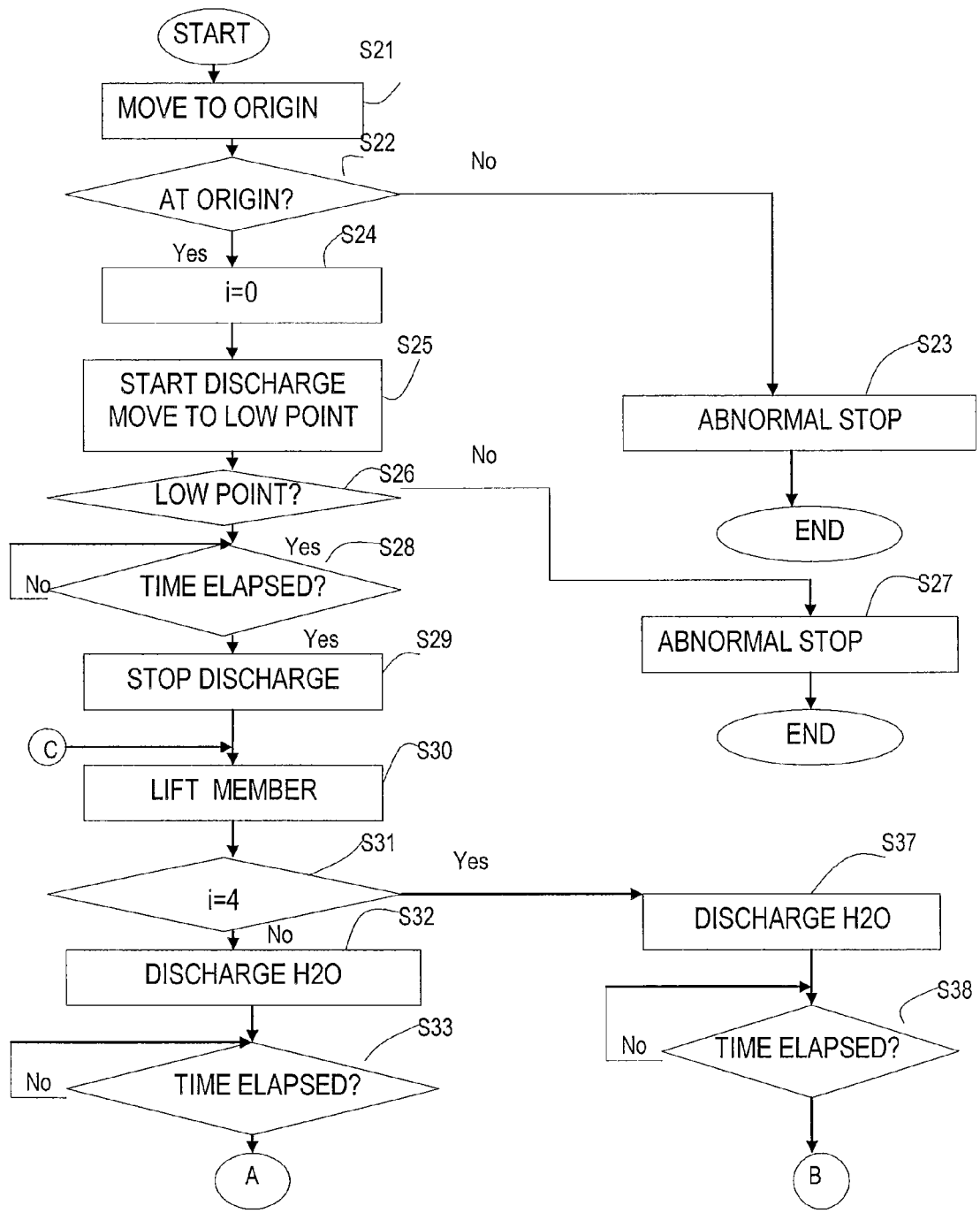
FIG. 16 is a flow chart (first half) describing the cleaning process of the cell analyzer of the embodiment of the present invention.

In step S8, in a branching from the main process, the cleaning process is performed on the used first container 150. That is, the preparation controller 23 controls the first container cleaning section 46 to clean the first container 150. Specifically, after the process of step S7, the preparation controller 23 rotates the first reaction unit 43 clockwise, and moves the first container 150 to the position corresponding to the first cleaning section 46. The preparation controller 23 then controls the first container cleaning section 46 to clean the first container 150. Note that the first container 150 cleaning process in step S8 will be described in detail in subsequent steps S21 through S46 (refer to FIGS. 16 and 17).

In step S9, the preparation controller 23 controls the replacement unit 48 to perform the discrimination and replacement process on the biological sample. In step S10, the preparation controller 23 switches the biological sample to the second sample pipette unit 47.

In step S11, the preparation controller 23 controls the container mover 51 to move the second container 250 to the second dispersing unit 49, and controls the second dispersing unit 49 to perform the second dispersing process. When the second dispersing process is completed, the preparation controller 23 moves the second container 250 to the liquid removal unit 50, and eliminates the water droplets adhered to the outer surface of the second container 250. Thereafter, the preparation controller 23 controls the container mover 51 to move the second container 250 to the second reaction unit 52.

In step S12, the preparation controller 23 controls the second reagent adding unit 53 to add RNase, and heats the second reaction unit 52 to perform the RNA removal process. In step S13, the preparation controller 23 controls the third reagent adding unit 54 to add staining solution, and heats the second reaction unit 52 to perform the DNA staining process.

In step S14, the preparation controller 23 controls the second suctioning unit 55 to dispense the stained measurement sample, and the measurement controller 13 controls the main detecting section 11 to perform the main measurement.

In step S15, the preparation controller 23 controls the second container cleaning section 56 to perform the cleaning process on the second container 250. Thereafter, the CPU 2a ends the cell analysis process. Note that the second container 250 cleaning process in step S15 will be described in detail in subsequent steps S21 through S46.

The cleaning process of the cell analyzer 1a is described below with reference to FIGS. 3 through 5, 7, 16, and 17. Note that operational control of the first container cleaning section 46 of the measurement device 1 is executed by the fluid controller 114 or drive controller 134, and the operational control of the second container cleaning section 56 of the measurement device 1 is executed by the fluid controller 214 or drive controller 234. Note that since operational control of the second container cleaning section 56 is identical to the operational control of the first container cleaning section 46, and only the operational control of the first container cleaning section 46 is described below.

In step S21, the drive controller 134 controls the drive unit 131 to move the discharge member 100 to the origin position.

In step S22, the drive controller 134 determines whether the discharge member 100 has moved to the origin position. Specifically, the drive controller 134 advances the process to step S24 when the movement of the discharge member 100 to the origin position is detected by the origin sensor 132. The drive controller 134 advances the process to step S23 when the movement of the discharge member 100 to the origin point is not detected (that is, when the discharge member 100 has not moved to the origin position).

In step S23, the CPU 2a abnormally stops the cell analyzing apparatus 1a. Specifically, the ongoing processing of the current biological sample continues, but the processing of subsequent samples is stopped.

When the process advances to step S24, the drive controller 134 resets the number of cleanings i to [0].

In step S25, the fluid controller 114 starts the discharge operation by the suction device 120, and the drive controller 134 controls the drive unit 131 to move the discharge member 100 to the lowest point. As a result, sample in the first container 150 is discharged from the discharge flow path 107 while the elevator device 130 lowers the discharge member 100.

In step S26, the drive controller 134 determines whether the discharge member 100 has moved to the lowest point. Specifically, the drive controller 134 advances the process to step S28 when the movement of the discharge member 100 to the lowest point is detected by the low point sensor 133. The drive controller 134 advances the process to step S27 when the movement of the discharge member 100 to the lowest point is not detected by the low point sensor 133 (that is, when the discharge member 100 has not moved to the lowest point). In step S27, the drive controller 134 performs processing identical to the processing of step S23.

When the process advances to step S28, the fluid controller 114 determines whether a predetermined time has elapsed. Specifically, the fluid controller 114 repeats the determination as to whether a predetermined time has elapsed (for example, 1.5 seconds) after the discharge member 100 has moved to the low point as the sample discharge continues, and the process advances to step S29 when the predetermined time has elapsed.

In step S29, the fluid controller 114 stops the discharge operation by the suction device 120. In step S30, the drive controller 134 controls the drive unit 131 to raise the discharge member 100 a predetermined amount (for example, 8 mm).

In step S31, the drive controller 134 determines whether number of cleanings i is [4]. When the number of cleanings i is [4], the drive controller 134 advances the process to step S37. When the number of cleanings i is not [4], the drive controller 134 advances the process to step S32.

In step S32, the fluid controller 114 controls the discharge unit 110a to discharge the distilled water. Thus, the distilled water is discharged from the discharge unit 110a while the discharge member 100 is distanced a predetermined amount above the deepest part 150b of the first container 150.

In step S33, the fluid controller 114 determines whether a predetermined time has elapsed. Specifically, the fluid controller 114 repeats the determination whether a predetermined time (for example, 1.5 seconds) has elapsed since the discharge unit 110*a* discharged the distilled water until the predetermined time has elapsed, then the process advances to step S34.

Figure 17:
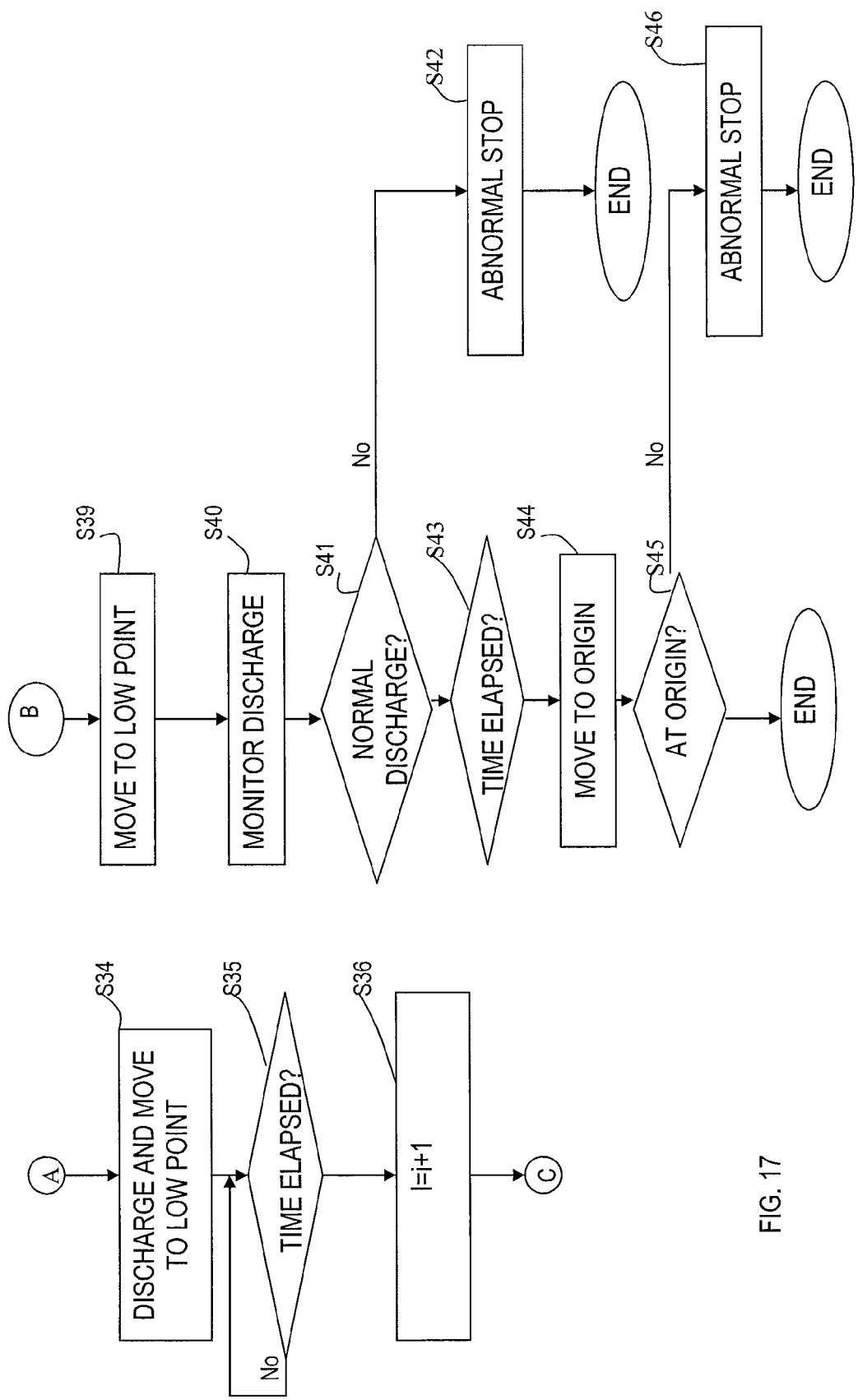
FIG. 17 is a flow chart (second half) describing the cleaning process of the cell analyzer of the embodiment of the present invention.

In step S34 of FIG. 17, the fluid controller 114 starts the discharge operation by the suction device 120, and the drive controller 134 controls the drive unit 131 to move the discharge member 100 to the lowest point. Specifically, distilled in the first container 150 is discharged from the discharge flow path 107 while the elevator device 130 lowers the discharge member 100.

When the process advances to step S35, the fluid controller 114 determines whether a predetermined time has elapsed. Specifically, the fluid controller 114 repeats the determination as to whether a predetermined time has elapsed (for example, 1.5 seconds) after the discharge member 100 has moved to the low point, and the process advances to step S36 when the predetermined time has elapsed.

In step S36, the drive controller 134 increments the number of cleanings i by [1], and the process returns to step S30.

When the number of cleanings reaches [4], the fluid controller 114 controls the discharge unit 110*a* to discharge the diluting liquid.

In step S38, the fluid controller 114 determines whether a predetermined time has elapsed. Specifically, the fluid controller 114 repeats the determination whether a predetermined time (for example, 1.5 seconds) has elapsed since the discharge unit 110*a* discharged the diluting liquid until the predetermined time has elapsed, then the process advances to step S39.

In step S39, the drive controller 134 controls the drive unit 131 to move the discharge member 100 to the lowest point.

In step S40, the fluid controller 114 starts the discharge operation by the suction device 120, and monitors the discharge status via the suction sensor 122. The fluid controller 114 monitors whether the diluting liquid is flowing normally within the discharge tube 121.

In step S41, the fluid controller 114 determines whether the discharge status is normal. When the discharge status is normal, the fluid controller 114 advances the process to step S43. When the discharge status is not normal, the fluid controller 114 advances the process to step S42. In step S42, the drive controller 134 performs processing identical to the processing of step S23.

When the process advances to step S43, the fluid controller 114 determines whether a predetermined time has elapsed. Specifically, the fluid controller 114 repeats the determination as to whether a predetermined time has elapsed (for example, 1.5 seconds) after the discharge member 100 has moved to the low point, and the process advances to step S44 when the predetermined time has elapsed.

In step S44, the drive controller 134 controls the drive unit 131 to move the discharge member 100 to the origin position.

In step S45, the drive controller 134 determines whether the movement of the discharge member 100 to the origin position has been detected by the origin sensor 132. The drive controller 134 advances the process to step S46 when the discharge member 100 has not moved to the origin position. In step S46, the drive controller 134 performs processing identical to the processing of step S23. However, the preparation controller 23 ends the cleaning process when the discharge member 100 has moved to the origin position.

The following effects are obtained in the present embodiment.

In the embodiment described above, the amount of cleaning liquid used to clean the container is inhibited from increasing by forming bottom part 101 (201) of the discharge member 100 (200) in a shape that conforms to the substantially spherical inner bottom part of the first container 150 (second container 250) so as to be inserted into the deepest part 150*b* (250*b*) of the first container 150 (second container 250) and reducing the volume of the discharge member 100 (200) immersed in the cleaning liquid. The first container 150 (second container 250) can be sufficiently cleaned because the gap is reduced between the first container 150 (second container 250) and the bottom part 101 (201) of the discharge member 100 (200) and the circulation speed of the cleaning liquid is increased. Therefore, carry over can be reduced while inhibiting an increase in the amount of cleaning liquid being used. Furthermore, the amount of cleaning liquid needed to clean the first container 150 (second container 250) can be reduced because the volume of the discharge member immersed in the cleaning liquid can be increased by configuring the discharge member to be insertable to the deepest part 150*b* (250B) of the first container 150 (second container 250).

In the above embodiment, the channels 106 (206) are configured to guide the sample or cleaning liquid to the aperture 105 (205). The channels 106 (206) also are configured to connect to the aperture 105 (205). Sic channels 106 (206) extend radially at substantially equiangular intervals around the aperture 105 (205). The channels 106 (206) extend from the aperture 105 (205) to the vicinity of the end part 102*a* (202*a*) of the body portion 102 (202) on the bottom side 101 (201). The channels 106 (206) have a width W1 (W2) which is smaller than the internal diameter D1 (D3) of the aperture 105 (205). The discharge member 100 (200) is configured so that the gap between the bottom portion 101 (201) inserted into the first container 150 (second container 250), and the inner wall surface 150*a* (250*a*) of the first container 150 (second container 250) gradually narrows toward the deepest part 150*b* (250*b*) of the first container 150 (second container 250). Accordingly, the channel 106 (206) guides the sample or cleaning liquid to the aperture 105 (205) to reliably discharge the sample or the cleaning liquid from the discharge flow path 107 (tube 207) even when discharging cleaning liquid while the bottom part 101 (201) of the discharge member 100 (200) is stuck to the bottom of the first container 150 (second container 250). Thus, the sample or cleaning liquid can be efficiently guided to the aperture 105 (205) by the six channels 106 (206). Hence, sample or cleaning liquid is easily guided through the channels 106 (206) to the aperture 105 (205) even when there is a narrow space between the body portion 102 (202) and the inner wall surface 150*a* (250*a*) of the first container 150 (second container 250). The force is increased during the discharge of the sample or the cleaning liquid accumulated in the channels 106 (206) so as to efficiently guide the liquid to the aperture 105 (205). The force is increased during the discharge of the sample or the cleaning liquid in the vicinity of the deepest part 150*b* (250*b*) of the first container 150 (second container 250) so as to efficiently guide the liquid to the aperture 105 (205).

In the present embodiment, the discharge portion 110*a* (discharge device 110) is provided to discharge cleaning liquid so as to flow along the conical frustum shaped inclined portion 103. Therefore, the cleaning liquid can be uniformly circulated within the first container 150 even with the provision of the discharge member 100 by inducing the cleaning liquid discharged from the discharge portion 110*a* to flow in a downward inclined direction on the conical frustum shaped inclined portion 103.

In the present embodiment, the discharge flow path 107 (tube 207) is configured to discharge sample or cleaning liquid into the first container 150 (second container 250) while the discharge member 100 (200) is lowered by the elevator device 130 (230). Leakage caused by lowering the discharge member 100 (200) into the first container 150 (second container 250) of the sample or cleaning liquid is therefore reliably prevented.

The present embodiment provides a discharge device 110 (210) for discharging cleaning liquid to the first container 150 (second container 250) while the discharge member 100 (200) is distanced from the deepest part 150b (250b) of the first container 150 (second container 250), and the discharge member 100 (200) is configured to lower the discharge member 100 (200) to the deepest part 150b (250b) of the first container 150 (second container 250) after the cleaning liquid is discharged into the first container 150 (second container 250). The first container 150 (second container 250) is therefore sufficiently cleaned by circulating the cleaning liquid within the first container 150 (second container 250).

In the present embodiment, the discharge flow path 107 is integratedly provided with the discharge member 100. The integrated configuration of the discharge member 100 and the discharge flow path 107 therefore reduces the number of components. The tubular nozzle of the tube 207 also is provided on the discharge member 200. The discharge member 100 (200) is inserted into the first container 150 (second container 250) so that the center axis C1 of the first container 150 (second container 250) matches the center axis C2 of the discharge member 100 (200). The discharge member 100 (200) therefore is easily inserted into the first container 150 (second container 250).

Note that the embodiment of the present disclosure is an example in all aspects and not to be considered limiting in any way. The scope of the present invention is expressed by the scope of the claims and not by the description of the embodiment, and includes all meanings and equivalences and modifications pertaining thereunto.

For example, although the above embodiment is described by way of example wherein the present invention is applied to a cell analyzer for analyzing epithelial cell of the cervix, the present invention is not limited to this application. The present invention is also applicable to other kinds of analyzers.

Although the discharge member 100 of the first container cleaning section 46 and the discharge member 200 of the second container cleaning section 56 are described by way of example in the above embodiment as having respectively different shapes, the present invention is not limited to this configuration. In the present invention, the discharge member 100 of the first container cleaning section 46 and the discharge member 200 of the second container cleaning section 56 may have the same shape.

Figure 18:
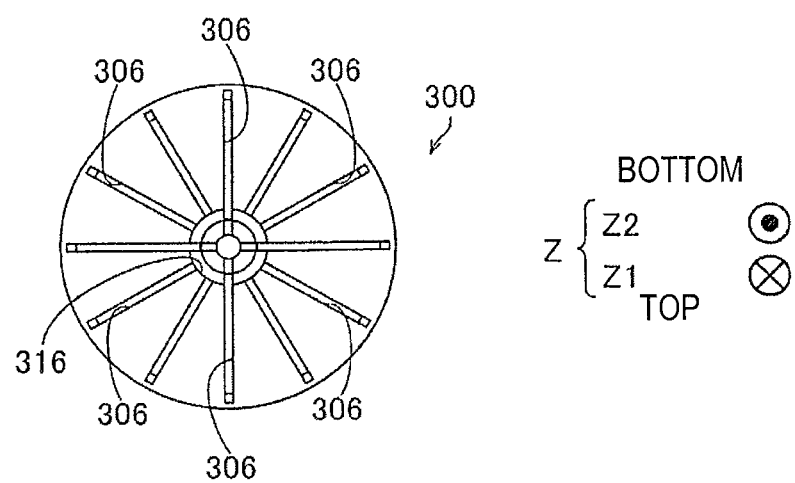
FIG. 18 is a view from the bottom side of a modification of the discharge member of the cell analyzer of the embodiment of the present invention.

Although the above embodiment is described by way of example of providing six channels on the discharge member, the present invention is not limited to this number. In the present invention, the channels 306 provided on a discharge member 300 may number one or more, or five or fewer, or seven or more. An example of the discharge member 300 provided with twelve channels 306 is shown in FIG. 18.

Although the above embodiment is described by way of example of providing linear channels on the discharge member, the present invention is not limited to this configuration. In the present invention, the discharge member 300 also may be provided with nonlinear channels 316 in addition to linear channels 306. For example, the discharge member 300 has linear channels 306 and circular channels 316, as shown in FIG. 18.

Although the above embodiment is described by way of example of providing channels of fixed width on the discharge member, the present invention is not limited to this configuration. In the present invention, the channel width need not be fixed.

Although the above embodiment is described by way of example of providing a discharge flow path 107 as a tubular discharge hole integrated with the discharge member 100, the present invention is not limited to this configuration. In the present invention, the discharge member 100 may be provided with a flow path 107 separate from the discharge member 100. Although the example describes the tube 207 as a tubular nozzle provided on the discharge member 200, the present invention is not limited to this configuration. In the present invention, the tube 207 discharge hole provided on the discharge member also may be configured integratedly with the discharge member 200.

Although the above embodiment is described using a flow-driven flow for performing processes sequentially along the processing flow of the controller to facilitate understanding, the processes of the controller also may be performed by an event-driven process which executes processes in event units. In this case, all processes may be event-driven or a combination of event-driven and flow-driven.

Although the discharge member 200 is described as having a body portion in the above embodiment, the present invention is not limited to this configuration. In the present invention, the discharge member 200 also may be configured by an inclined portion and bottom portion which do not have a body portion.

What is claimed is:

1. A container cleaning device which cleans a container for holding a sample, comprising:
  an extended discharge member which comprises a body having a hollow tubular discharge flow path which connects to an aperture at an end of a bottom portion of the body, wherein the extended discharge member is insertable into a container having a substantially hemispherical shaped inner bottom, wherein:
    the extended discharge member is shaped to guide liquid which flows along the extended discharge member to the aperture,
    the bottom portion of the extended discharge member is also substantially hemispherical shaped to enable the extended discharge member to be inserted close to the substantially hemispherical shaped inner bottom of the container,
    a plurality of engraved channels are radially extended out from the aperture, which extend upward along the bottom portion of the extended discharge member to help guide the liquid which flows down along the extended discharge member to the aperture; and
  a cleaning nozzle disposed adjacent to an upper portion of the extended discharge member to dispense a cleaning liquid into the container, wherein the dispensed cleaning liquid is guided to flow down along the extended discharge member to the aperture through the plurality of engraved channels.

2. The container cleaning device of claim 1, wherein the plurality of engraved channels are formed to extend radially out at substantially equiangular intervals from around the aperture.

3. The container cleaning device of claim 1, wherein the extended discharge member comprises a body portion which has a cylindrical shape, and the plurality of engraved channels are formed to extend from the aperture to the body portion.

4. The container cleaning device of claim 1, wherein
the aperture has a substantially circular shape; and
a width of the engraved channel is less than an inner diameter of the aperture in planar view.

5. The container cleaning device of claim 1, wherein the extended discharge section member comprises an inclined portion having the a shape of a frustum of a cone which has a decreasing diameter in an upward direction, and
the cleaning nozzle is configured to discharge dispense the cleaning liquid to the inclined portion so as to flow along the inclined portion of the conical frustum when the discharge section is inserted in the container.

6. The container cleaning device of claim 1, further comprising an elevator device configured to uplift and lower the extended discharge on member;
a suctioning device connected to the hollow tubular discharge flow path to evacuate the samples in the container while the extended discharge member is being lowered by the elevator device.

7. The container cleaning device of claim 6, further comprising a controller programmed to:
cause the elevator device to lift the extended discharge member so that the extended discharge member is distanced upward from a deepest part of the inner bottom of the container when the cleaning nozzle dispenses the cleaning liquid into the container; and
cause the elevator device to lower the extended discharge member to the deepest part of the inner bottom of the container after the cleaning liquid is dispensed.

8. The container cleaning device of claim 1, wherein
the hollow tubular flow path is integratedly formed within the extended discharge member.

9. The container cleaning device of claim 1, wherein the discharge tubular hollow discharge flow path comprises a tubular nozzle, and
the tubular nozzle is fixedly inserted into the body of the extended discharge member so as to be connected to the aperture.

10. The container cleaning device of claim 1, wherein
the extended discharge member is formed in a substantially circular shape in a horizontal cross section.

11. The container cleaning device of claim 1, further comprising
a suctioning device which is connected to the hollow tubular discharge flow path and suctions the samples or the cleaning liquid in the container through the aperture and the hollow tubular discharge flow path.

12. An extended discharge member for a container cleaning device for cleaning a container having a substantially hemispherical shaped inner bottom, the discharge member comprising:
a body having a hollow tubular discharge flow path which connects to an aperture disposed at an end of a bottom portion, wherein the extended discharge member is insertable into the container having the substantially hemispherical shaped inner bottom;
wherein the extended discharge member is shaped to guide liquid which flows down along the extended discharge member to the aperture;
wherein the bottom portion of the extended discharge member is also substantially hemispherical shaped to enable the extended discharge member to be inserted close to the substantially hemispherical shaped inner bottom of the container;
a plurality of engraved channels are radially extended out from the aperture, which extend upward along the bottom portion of the extended discharge member to help guide the liquid which flows down along the extended discharge member to the aperture at the deepest part of the container.

13. An analyzer comprising:
a controller;
memory including stored programmable codes;
at least a processor that executes the programmable codes stored in the memory, which configures the controller to cause the analyzer to prepare a measurement sample by conducting in a container a predetermined processing of a biological sample collected from a subject;
an extended discharge member which comprises a body having a hollow tubular discharge flow path which connects to an aperture at an end of a bottom portion, wherein the extended discharge member is insertable into a container having a substantially hemispherical shaped inner bottom, wherein:
the extended discharge member is shaped to guide liquid which flows along a path on the extended discharge member to the aperture,
the bottom portion of the extended discharge member is also substantially hemispherical shaped to enable the extended discharge member to be inserted close to the substantially hemispherical shaped inner bottom of the container,
a plurality of engraved channels are radially extended out from the aperture, which extend upward along the bottom portion of the extended discharge member to help guide the liquid which flows down the extended discharge member to the aperture; and
a cleaning nozzle disposed adjacent to an upper portion of the extended discharge member to dispense a cleaning liquid into the container, wherein the dispensed cleaning liquid is guided to flow down along the extended discharge member to the aperture through the plurality of engraved channels.

14. A container cleaning device which cleans a container for holding a sample, comprising:
an extended discharge member which comprises a body having a hollow tubular discharge flow path which connects to an aperture at an end of a bottom portion, wherein the extended discharge member is insertable into a container having a substantially hemispherical shaped inner bottom, wherein:
the extended discharge member is shaped to guide liquid which flows along a path on the extended discharge member to the aperture,
the bottom portion of the extended discharge member is also substantially hemispherical shaped to enable the extended discharge member to be inserted close to the substantially hemispherical shaped inner bottom of the container,
a plurality of engraved channels are radially extended out from the aperture, which extend upward along the bottom portion of the extended discharge member to help guide the liquid which flows down the extended discharge member to the aperture; and
a cleaning nozzle disposed adjacent to an upper portion of the extended discharge member to dispense a cleaning liquid into the container, wherein the dispensed cleaning liquid is guided to flow down along the extended discharge member to the aperture through the plurality of engraved channels;
the aperture has a substantially circular shape; and
a width of the engraved channel is less than an inner diameter of the aperture in planar view.

* * * * *